United States Patent
Buvat et al.

(10) Patent No.: US 9,421,531 B2
(45) Date of Patent: Aug. 23, 2016

(54) METHOD FOR PREPARING PROTON-CONDUCTING PARTICLES CAPABLE OF CATALYZING THE REDUCTION OF OXYGEN OR THE OXIDATION OF HYDROGEN

(71) Applicants: Commissariat a l'energie atomique et aux energies alternatives, Paris (FR); Centre National de la Recherche Scientifique, Paris (FR)

(72) Inventors: Pierrick Buvat, Montbazon (FR); Anne-Claire Ferrandez, Colleville Montgomery (FR); Steve Baranton, Poitiers (FR); Christophe Coutanceau, Poitiers (FR)

(73) Assignees: COMMISSARIAT A L'ENERGIE ATOMIQUE ET AUX ENERGIES ALTERNATIVES, Paris (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 104 days.

(21) Appl. No.: 14/356,420

(22) PCT Filed: Nov. 5, 2012

(86) PCT No.: PCT/EP2012/071858
§ 371 (c)(1),
(2) Date: May 6, 2014

(87) PCT Pub. No.: WO2013/068318
PCT Pub. Date: May 16, 2013

(65) Prior Publication Data
US 2014/0309386 A1 Oct. 16, 2014

(30) Foreign Application Priority Data
Nov. 7, 2011 (FR) .................................... 11 60115

(51) Int. Cl.
B01J 31/12 (2006.01)
C08F 2/38 (2006.01)
C08F 292/00 (2006.01)
C07C 323/41 (2006.01)
H01M 4/90 (2006.01)
H01M 4/92 (2006.01)
H01M 8/10 (2016.01)

(52) U.S. Cl.
CPC ............ B01J 31/123 (2013.01); C07C 323/41 (2013.01); C08F 2/38 (2013.01); C08F 292/00 (2013.01); H01M 4/9008 (2013.01); H01M 4/926 (2013.01); C08F 2438/01 (2013.01); H01M 2008/1095 (2013.01); Y02E 60/50 (2013.01)

(58) Field of Classification Search
CPC ..................................................... B01J 31/123
See application file for complete search history.

(56) References Cited

U.S. PATENT DOCUMENTS 7,037,596 B1 * 5/2006 Benthien .................. A61L 9/01
428/334
2008/0004175 A1 * 1/2008 Aoshima ................ B01J 31/123
502/159

OTHER PUBLICATIONS

Gal, et al. ("Water-Soluble Polymer-Grafted Platinum Nanoparticles for the Subsequent Binding of Enzymes. Synthesis and SANS." Journal of Polymer Science Part A: Polymer Chemistry. vol. 50 No. 2. Oct. 14, 2011. pp. 289-296).*
Li, et al. ("Fabrication of pH-Responsive Nanocomposites of Gold Nanoparticles/Poly(4-vinylpyridine)", Chem. Mater. 2007, vol. 19, pp. 412-417).*
Li, et al., "Fabrication of pH-Responsive Nanocomposites of Gold Nanoparticles/Poly(4-vinylpyridine)", Chem. Mater., Jan. 13, 2007.
Carrot et al., "Polymer-Grafted-Platinum Nanoparticles: From Three-Dimensional Small-Angle Neurton Scattering Study to Tunable Two-Dimensional Array Formation", Langmuir, vol. 25, No. 1, Jan. 1, 2009.
Gal, et al., "Water-Soluble Polymer-Grafted Platinum Nanoparticles for the Subsequent Binding of Enzymes. Synthesis and SANS", Journal of Polymer Science Part A: Polymer Chemistry, vol. 50, No. 2, Oct. 14, 2011.
International Search Report issued in Application No. PCT/EP2012/071858 dated Jun. 5, 2013.
French Search Report issued in Application No. 1160115 dated Jul. 4, 2012.
Written Opinion issued in Application No. PCT/EP2012/071858 dated Jun. 5, 2013.

* cited by examiner

*Primary Examiner* — Ling Choi
*Assistant Examiner* — Lanee Reuther
(74) *Attorney, Agent, or Firm* — Pearne & Gordon LLP

(57) ABSTRACT

A method for preparing particles includes a material capable of catalyzing the reduction of oxygen or the oxidation of hydrogen, the particles being functionalized by polymers including at least one repeating unit bearing at least one proton-conducting group, and the particles being covalently bonded to a carbon material. The method includes the following consecutive steps: a) a step of contacting particles, comprising a material capable of catalyzing the reduction of oxygen or the oxidation of hydrogen, with a compound that is an initiator for ATRP polymerization, the compound comprising at least one group capable of being grafted onto the surface of the particles, whereby particles, onto which a radical of the initiator compound is grafted, are obtained; and b) a step of contacting the particles obtained in a) with at least one monomer having at least one proton-conducting group, whereby the polymerization of the monomer from the above-mentioned radicals occurs.

9 Claims, No Drawings

METHOD FOR PREPARING PROTON-CONDUCTING PARTICLES CAPABLE OF CATALYZING THE REDUCTION OF OXYGEN OR THE OXIDATION OF HYDROGEN

TECHNICAL FIELD

The present invention relates to a method for preparing specific particles capable of catalyzing the reduction of oxygen or the oxidation of hydrogen, said particles being, in addition, proton-conducting thanks to a functionalization of said particles with proton-conducting organic polymers.

The present invention also relates to the particles obtained by said method.

Said particles have the characteristic of exhibiting catalytic activity (in particular, for the oxidation of hydrogen or the reduction of oxygen) while having proton conductivity.

Consequently, said particles find their application in the elaboration of electrode materials, in particular materials intended to enter into the constitution of catalytic layers of electrodes for fuel cells, such as fuel cells operating with $H_2$/air or $H_2/O_2$ (known under the abbreviation PEMFC signifying "Proton Exchange Membrane Fuel Cell").

Thus, the present invention lies in the field of fuel cells operating on the principle of the oxidation of hydrogen and the reduction of oxygen.

STATE OF THE PRIOR ART

A fuel cell of this type is an electrochemical generator, which converts chemical energy into electrical energy thanks to two electrochemical reactions: an oxidation reaction at the anode of a fuel (hydrogen) combined with a reduction reaction at the cathode of an oxidant (air or oxygen).

Conventionally, this type of fuel cell comprises a plurality of electrochemical cells mounted in series, each cell comprising two electrodes of opposite polarity separated by a proton exchange membrane serving as solid electrolyte, said membrane assuring the passage to the cathode of the protons formed, by electrochemical reaction, during the oxidation of the fuel at the anode.

The aforementioned electrochemical reactions (oxidation and reduction) take place at specific zones of the electrodes (known as active zones corresponding structurally to catalytic layers), which form the junction between the diffusion layer (at the level of which the supply of reagents takes place) of the electrodes and the membrane and requiring, to take place, the use of catalysts, which consist, conventionally, for PEMFC type fuel cells, of platinum particles.

Given the costs implied by the presence of a catalyst such as platinum, it is advisable to obtain a maximum catalytic surface for a given weight of metal, such an objective being able to be attained by platinum particles of nanometric sizes (also designated platinum nanoparticles).

It is also advisable, so that the electrochemical reactions can take place, that the platinum particles are in contact both with the fuel or the oxidant (according to whether one is situated at the anode or the cathode), the proton conductor constituting the membrane and the electron conductor entering into the constitution of the electrode (said electron conductor being conventionally a carbon material), said contact zone being known as the triple point, whereby the greater the number of triple points the more efficient the electrode.

In other words, in these triple points, at the level of the platinum particles there is:

a physical continuity with the electrolytic membrane, to assure a conduction of protons H+;
a physical continuity with the electron conductor, to assure the conduction of electrons; and
a physical continuity with the diffusion zone of the electrodes, to assure the diffusion of gases (oxygen or hydrogen for PEMFC fuel cells).

The maintaining over time of these triple points assumes the respect of the integrity of the contact zones between the different elements entering into the constitution of these triple points, which implies maintaining the physical integrity of these different elements, in particular platinum particles.

However, certain studies have shown that it is possible to witness, during the operation of a fuel cell, a degradation of the platinum particles (resulting, consequently, in a reduction of the active surface) either by phenomena of dissolution or by phenomena of increasing the sizes of the particles (stemming, conventionally, from agglomeration phenomena).

These dissolution phenomena can take place with fuel cells operating at very low pH (for example, a pH below 1) and at high operating potentials at the cathode (for example, a potential above 1 V with respect to RHE (RHE signifying reversible hydrogen electrode), the dissolved platinum being able to be found either in the water formed during the operation of the fuel cell or within the electrolytic membrane, generally, polymeric, which leads, therein, to the formation of inactive platinum nanocrystals.

As for size increase phenomena, they can take place with fuel cells in which the platinum nanoparticles have high mobility at the surface of the support, generally carbon, on which they are deposited, this mobility depending on the surface energy thereof.

To overcome these phenomena, resort may be made to high loading levels of platinum particles, with the drawbacks which that represents in terms of production costs, in light of the very high price of platinum on markets.

In order to reduce loading levels while attaining an efficient active surface, studies have focused on the optimization of electrode (here, comprising platinum particles)—membrane assemblies.

Thus, it has been proposed to juxtapose, by intimate contact, the different elements (platinum particles, electrical conductor and electrolyte) required for the creation of the triple points, this juxtaposition being able to consist in:

mixing platinum particles with carbon powder (fulfilling the role of electrical conductor) and impregnating the whole with electrolyte, so as to guarantee better contact with the membrane;
depositing, by thin film deposition techniques (such as electro-deposition or sputtering by physical process), platinum particles, which makes it possible to deposit platinum at low concentrations while maintaining very high catalytic activity.

Nevertheless, the assemblies resulting from these techniques are fragile due to the weak bonds involved in juxtaposing the constituent elements of said assemblies, which does not make it possible to prevent phenomena of degradation due to the migration of platinum particles leading to, as a result, a reduction in the lifetime of said assemblies.

In light of the preceding, the authors of the present invention set themselves the objective of proposing a method for manufacturing particles comprising a material capable of catalyzing the oxidation of hydrogen or the reduction of hydrogen, which particles are bound to a proton conductor (to be specific proton-conducting polymers) and, potentially to an electron conductor (such as a carbon material) by stronger bonds than the assemblies existing in the prior art, so as to improve the durability of the triple points, when said particles are intended to be used for the constitution of catalytic layers of PEMFC type fuel cells.

DESCRIPTION OF THE INVENTION

Thus, the invention relates to a method for preparing particles comprising a material capable of catalyzing the reduction of oxygen or the oxidation of hydrogen, said particles being functionalized by polymers comprising at least one repeating unit having at least one proton-conducting group and said particles being bound, for example, by covalence, to a carbon material, said method comprising the following consecutive steps:

a) a step of contacting particles comprising a material capable of catalyzing the reduction of oxygen or the oxidation of hydrogen with a compound that is an initiator for ATRP polymerization, which compound comprises at least one group capable of being grafted onto the surface of said particles, whereby particles, onto which a radical of said initiator compound is grafted, are obtained;

b) a step of contacting said particles obtained in a) with at least one monomer having at least one proton-conducting group, whereby there is polymerization of said monomer from the above-mentioned radicals.

Before going into greater detail in the present description, the following definitions are defined.

Polymer is conventionally taken to mean, according to the invention, a compound constituted of the sequencing of one or more repeating units.

Repeating unit is conventionally taken to mean, according to the invention, a bivalent organic group (i.e. a group forming a bridge) derived from a monomer after polymerization thereof.

ATRP polymerization is taken to mean a radical polymerization by transfer of atoms (ATRP corresponding to "Atom Transfer Radical Polymerization"). The mechanism of this type of polymerization will be given in greater detail below.

Compound that is an initiator for ATRP polymerization is taken to mean a compound comprising at least one group capable of initiating this type of polymerization, the polymerization initiator compound according to the invention comprising, moreover, a group capable of being grafted onto the surface of the aforementioned particles, which signifies in other words, that this group reacts in the presence of the particles to be fixed by covalence to the surface thereof (one may thus speak of grafting), whereby the initiator remains at the surface of the particles in the form of a radical, it being understood that said radical further comprises at least one group capable of initiating an ATRP polymerization.

Thus, thanks to the implementation of the method of the invention, it is thereby possible to obtain particles comprising a material capable of catalyzing the reduction of oxygen or the oxidation of hydrogen grafted by covalence via a radical of initiator compound by proton-conducting polymers, which enables, when said particles are intended to enter into the constitution of electrodes (in particular at the level of the catalytic layers thereof) good physical continuity to be assured with the adjacent electrolyte, when it is also based on proton-conducting polymer(s).

As mentioned below, the method of the invention comprises a step of contacting particles comprising a material capable of catalyzing the reduction of oxygen or the oxidation of hydrogen with a compound that is an initiator for ATRP polymerization comprising a group capable of being grafted onto the surface of said particles, whereby particles, onto which a radical of said compound (step a) is grafted, are obtained.

This contacting step may comprise an operation of dispersion of the aforementioned particles followed by an operation of contacting the dispersion obtained with an initiator as defined above.

The particles comprising a material capable of catalyzing the reduction of oxygen or the oxidation of hydrogen may be metal particles, namely particles comprising one or more metal elements (in which case, when there are several metal elements, one could speak of particles made of metal alloy(s)).

Particularly suitable metal particles may be particles comprising a noble metal, such as platinum, ruthenium, palladium and mixtures thereof.

When the particles obtained according to the invention are intended to be used in PEMFC fuel cells, the metal particles are advantageously platinum particles.

The compound that is an initiator for ATRP polymerization is a compound comprising at least one group capable of initiating ATRP polymerization, i.e. a group capable of cleaving at a bond to form a first radical species and a second radical species, the first radical species reacting subsequently with a first carbon bearing a double bond belonging to the monomer implemented in step b), the second radical species fixing itself to a second atom opposite the first carbon bearing the double bond.

In other words, this mechanism may be summarized according to the following reaction scheme:

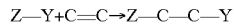

Z—Y corresponding to the aforementioned initiator with Z corresponding to the first species and Y corresponding to the second species.

For reasons of simplicity, only the double bond of the monomer involved in step b) has been represented above.

Moreover, the initiator compound used within the scope of the method of the invention comprises at least one group capable of being grafted onto the surface of the aforementioned particles, i.e. a group capable of reacting with the surface of said particles to form a covalent bond, whereby a radical of this initiator bound in a covalent manner to the surface of said particles remains.

The initiator compound used within the scope of the method of the invention may be an organic halide compound (namely, a compound comprising at least one halogen atom bound to a carbon atom, the resulting group being able to be symbolized by —C—X, X representing a halogen atom) comprising at least one group selected from —S—S— and —SH, —S—S— being a divalent disulfide group, i.e. a disulfide group forming a bridge between two other groups of the compound and —SH being a monovalent thiol group.

In this type of compound, the group capable of initiating ATRP polymerization is the —C—X group mentioned above, said group being able to cleave, in a homolytic manner, at the carbon-halogen bond to form two radical species, a first carbon radical species (being able to be symbolized by —C.) and a second radical species consisting of a halogen radical (being able to be symbolized by X.), the first species reacting with one end of the double bond of the monomer and the second species reacting with the opposite end of the double bond.

The group capable of being grafted onto the surface of the particles consists, for this type of compound, of a group selected from —S—S— and —SH.

When it is a disulfide group —S—S—, the initiator compound, in the presence of particles, is going to split into two organic radicals by homolytic cleavage of the bond between the two sulfur atoms, the two radicals consisting in radical species, the free electrons of said species being situated at the level of the sulfur atoms, said free electrons each combining with an electron present at the surface of the particles to form a covalent bond between the aforementioned radicals and the particles via the sulfur atoms.

When it is a thiol group —SH, the initiator compound, in the presence of the particles, reacts via this group with the surface of the particles to form a covalent bond therewith, whereby there remains of the initiator an organic radical grafted onto the surface of said particles, said radical being of identical formula to the initiator apart from the fact that the hydrogen atom bound to the sulfur atom is replaced by a covalent bond between the sulfur and a particle.

This type of compound is particularly adapted with a view to being grafted by covalence onto the surface of platinum particles.

Compounds meeting this specificity may be compounds comprising a disulfide group —S—S—, in particular, symmetrical compounds, i.e. compounds comprising a symmetry around the disulfide bond, which signifies, in other words, that the two portions of the compound situated on either side of the disulfide bond are identical.

More specifically, compounds meeting this specificity may be compounds comprising a disulfide group —S—S— forming a bridge between two portions of said compounds, at least one of said two portions comprising a phenyl group bearing an amide group —NH—CO—R$^1$, R$^1$ being a hydrocarbon group bearing at least one halogen atom (it is understood, in this case, that the amide group is bound to a carbon atom of the phenyl group via the nitrogen atom of the group —NH—).

The aforementioned two portions may be identical.

A particular compound meeting the definition given above may be a compound of formula (I) below:

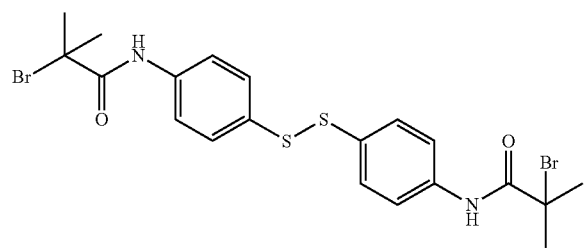

(I)

The symmetrical structure of this compound makes it possible to graft onto the surface of the particles a brominated mercaptoaniline radical present on either side of the disulfide group, which has the advantage of assuring a total grafting of the initiator compound to the surface of the particles.

This type of compound may be synthesized by an acylation reaction between an aminophenyl disulfide compound and an acyl chloride compound, in basic medium and organic solvent and in the potential presence of a catalyst, said acylation reaction taking place according to an addition-fragmentation mechanism.

As an example, when it involves preparing a compound of aforementioned formula (I), the acylation reaction may take place between a 4-aminophenyl disulfide compound and a bromoisobutyrate compound according to the following reaction scheme:

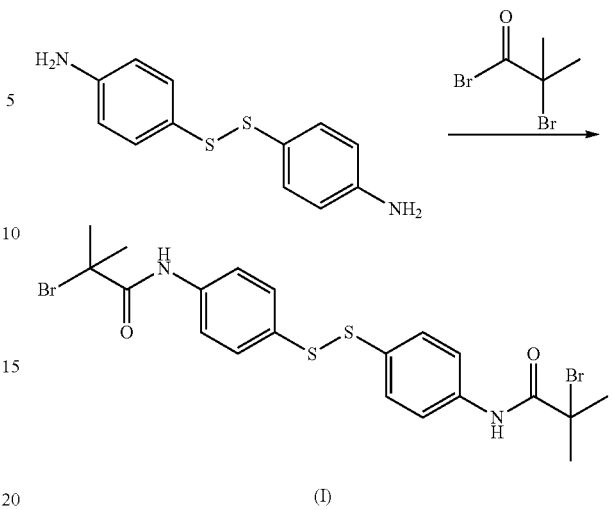

(I)

This reaction being able to be carried out with bipyridine as catalyst, chloroform as organic solvent, in a temperature range extending from 0° C. to room temperature.

The quantity of initiator compound brought into play during step a) may range from 0.5 to 20%, ideally 2 to 10% by weight with respect to the weight of the initiator compound, the particles and potentially the carbon material.

The method of the invention may comprise, before the implementation of step a), a step of preparing said aforementioned particles.

When the particles are metal particles, the preparation of the latter may consist in reducing a metal salt by reacting it with a reducing agent.

For example, when the metal particles are platinum particles, they may be prepared by reduction of a platinum salt with a reducing agent.

The platinum salt may be platinum halide salt, potentially hydrated, such as $H_2PtCl.6H_2O$.

The reducing agent may be metal hydride, and more particularly a metal borohydride, such as sodium borohydride (NaBH4).

The preparation may be carried out in a medium of the "oil-in-water" type, the oil being able to correspond to a hydrocarbon compound, such as hexane.

From a practical viewpoint, the preparation of platinum particles in such a medium may take place through the implementation of the following operations:

- an operation of contacting a platinum salt (for example, $H_2PtCl_6.6H_2O$) dissolved beforehand in water with a medium comprising an oil and potentially a dispersing agent (for example, tetraethylglycol dodecylether);
- an operation of adding to the mixture resulting from the preceding operation a reducing agent, in one or more steps, at the end of which the resulting mixture is stirred for a sufficient time up to the cessation of any release of gas (this cessation indicating that the reduction reaction has finished).

The mixture obtained thus comprises platinum particles, which mixture may be used as such for the implementation of step a) (it could thus be said that step a) is carried out in situ).

In a variant, the mixture obtained may be treated (for example, by filtration) so as to isolate the platinum particles obtained, the latter being intended to be used for the implementation of step a).

Apart from the fact that the particles obtained according to the method of the invention are functionalized by polymers comprising at least one repeating unit bearing at least one proton-conducting group, said particles are also bound, for example, by covalence, to a carbon material (being able to be assimilated with a carbon support), such as graphite, carbon black, carbon fibers, carbon tubes (such as carbon nanotubes), graphene and mixtures thereof.

The bonding of the particles to a carbon material may take place, according to variants, at different moments of the implementation of the method of the invention.

According to a first embodiment, the particles may be used already bound to a carbon material during the implementation of step a).

These particles already bound to a carbon material may be prepared prior to the step of implementation of step a).

In this case, the method of the invention may comprise, before the implementation of step a), a step of preparing particles comprising a material capable of catalyzing the reduction of oxygen or the oxidation of hydrogen bound to a carbon material.

According to a first variant, when the particles are metal particles, the preparation of the latter may comprise:
- an operation of reducing a metal salt by reacting it with a reducing agent, whereby metal particles are obtained;
- an operation of contacting the medium resulting from the preceding operation with the carbon material intended to be bound to the particles, whereby metal particles bound to a carbon material are obtained.

For example, when the metal particles are platinum particles, the reduction operation consists in reducing a platinum salt with a reducing agent.

The platinum salt may be a platinum halide salt, potentially hydrated, such as $H_2PtCl_6 \cdot 6H_2O$.

The reducing agent may be a metal hydride, and more particularly a metal borohydride, such as sodium borohydride (NaBH4).

The preparation may be carried out in a medium of the "oil-in-water" emulsion type, the oil being able to correspond to a hydrocarbon compound, such as hexane.

From a practical viewpoint, the preparation of platinum particles in such a medium, before contacting with the carbon material, can take place through the implementation of the following operations:
- an operation of contacting a platinum salt (for example, $H_2PtCl_6$-$6H_2O$), dissolved beforehand in water, with a medium comprising an oil and potentially a dispersing agent;
- an operation of adding to the mixture resulting from the preceding operation a reducing agent, at the outcome of which the resulting mixture is stirred for a sufficient time up to the cessation of any release of gas (this cessation indicating that the reduction reaction has finished), whereby a mixture comprising platinum particles is obtained.

This mixture comprising platinum particles is then contacted with the carbon material, preferably under ultrasounds, whereby, at the end of this contacting operation, a final mixture comprising platinum particles bound (for example by covalence) to the carbon material is obtained, which mixture may be used as such for the implementation of step a) (it could thus be said that step a) is carried out in situ).

In a variant, this mixture comprising platinum particles may be treated (for example, by filtration) so as to isolate the platinum particles obtained, the latter being intended to be used for the implementation of step a).

According to a second variant, when the particles are metal particles, the preparation may consist in a reduction step, by means of a reducing agent, of a mixture comprising a metal salt and a carbon material, by reacting it with a reducing agent, whereby metal particles bound to the carbon material are obtained.

For example, when the metal particles are platinum particles, the reduction step consists in reducing a platinum salt with a reducing agent.

The platinum salt may be a platinum halide salt, potentially hydrated, such as $H_2PtCl_6 \cdot 6H_2O$.

The reducing agent may be a metal hydride, and more particularly a metal borohydride, such as sodium borohydride ($NaBH_4$).

Even more specifically, the preparation of platinum particles bound to a carbon material may take place through the implementation of the following operations:
- an operation of contacting a basic aqueous solution (for example, based on lithium carbonate) of a platinum salt (for example, $H_2PtCl_6$—$H_2O$) with the carbon material;
- an operation of adding to the mixture resulting from the preceding operation a reducing agent, at the end of which the resulting mixture is stirred for a sufficient time until a mixture comprising platinum particles bound to the carbon material is obtained.

This mixture comprising platinum particles may be used as such for the implementation of step a) or may be treated (for example, by filtration) so as to isolate the platinum particles obtained, the latter being intended to be used for the implementation of step a).

According to a second embodiment, the particles may be used, during the implementation of step a), in a form not bound to the carbon material, which implies, in this case, that the method of the invention comprises, after step a) and before step b), a step of contacting the particles obtained at the end of step a) with the carbon material (designated hereafter step a'), whereby said particles are bound at the end of this step to the carbon material.

More specifically, this step of contacting with the carbon material may be carried out under ultrasounds, so as to activate the collision of the particles with the carbon material to form a bond between said particles and the material.

For the first embodiment (in other words the embodiment in which the particles are used already bound to a carbon material before the implementation of step a)), step a) may be carried out by the following operations:
- an operation of dispersing the particles in an electrophilic organic solvent, such as an amine solvent (like hexylamine), this type of solvent contributing to assuring good stabilization of the dispersion, whereby a dispersion of particles is obtained comprising a material capable of catalyzing the oxidation of hydrogen or the reduction of oxygen bound to a carbon material;
- an operation of contacting the aforementioned dispersion with an initiator compound as defined above, preferably dissolved beforehand in a solvent or mixture of solvents compatible with the solvent used for the dispersion (for example, an amine solvent/alcohol mixture, such as a hexylamine/methanol (50/50) mixture, when the dispersion solvent used is hexylamine), so as not to perturb the dispersion during the contacting operation;
- potentially, an operation of washing the particles obtained, for example, by precipitation/centrifugation cycles, so as to eliminate any traces of initiator compound not having reacted.

For the second embodiment (i.e. the embodiment for which the method of the invention comprises, after step a) and before step b), a step of contacting the particles obtained at the end of step a) with the carbon material (designated hereafter step a'), whereby said particles are bound at the end of this step to the carbon material), the method of the invention may comprise:

a step of preparing particles comprising a material capable of catalyzing the oxidation of hydrogen or the reduction of oxygen;

a step a), as defined above, of contacting, in the synthesis medium of the preceding step, an initiator compound for ATRP polymerization with the particles obtained beforehand;

a step of contacting particles derived from step a) with a carbon material, so as to obtain particles bound to a carbon material and grafted by radicals of initiator compound.

When the particles are metal particles, the step of preparing the latter may comprise an operation of reducing a metal salt by reacting it with a reducing agent, whereby metal particles are obtained.

For example, when the metal particles are platinum particles, the reduction step consists in reducing a platinum salt with a reducing agent.

The platinum salt may be a platinum halide salt, potentially hydrated, such as $H_2PtCl_6 \cdot 6H_2O$.

The reducing agent may be a metal hydride, and more particularly a metal borohydride, such as sodium borohydride (NaBH4).

The preparation may be carried out in a medium of "oil-in-water" emulsion type, the oil being able to correspond to a hydrocarbon compound, such as hexane.

From a practical viewpoint, the preparation of platinum particles in such a medium, before contacting the initiator compound then the carbon material, may take place by the implementation of the following operations:

an operation of contacting a platinum salt (for example, $H_2PtCl_6$—$H_2O$) dissolved beforehand in water with a medium comprising an oil and potentially a dispersing agent;

an operation of adding to the mixture resulting from the preceding operation a reducing agent, at the end of which the resulting mixture is stirred for a sufficient time up to the cessation of any release of gas (this cessation indicating that the reduction reaction has finished), whereby a mixture comprising platinum particles is obtained.

The step a) of contacting may take place by introducing the initiator compound into aqueous medium, so as not to perturb the synthesis medium of the particles.

The step of contacting with the carbon material may take place by introducing it directly into the synthesis medium and subjecting the resulting mixture to an ultrasonic treatment, so as to cause the bonding of the carbon material to the particles.

This embodiment makes it possible to carry out a one-pot synthesis of particles bound to a carbon material and grafted to radicals of initiator compound for ATRP polymerization.

Once step a) has been implemented and potentially step a'), the method of the invention comprises a step of contacting said particles obtained in a) with a monomer having at least one proton-conducting group, whereby there is polymerization of said monomer from the above-mentioned radicals, at the end of which there results particles functionalized by polymers comprising at least one repeating unit having at least one proton-conducting group, via radicals of initiator compound.

The proton-conducting group may be a sulfonic acid group —$SO_3H$, a carboxylic acid group —$CO_2H$ or a phosphonic acid group —$PO_3H_2$, said groups being able to be present potentially in the form of salts.

The monomers capable of being used within the scope of step b) may be all types of monomers compatible with ATRP polymerization and comprising at least one proton-conducting group potentially in the form of a salt.

Said monomers may in particular be chosen such that, after polymerization, they form polymer chains belonging to the family of polysulfones, polyetherketones, polyphenylenes, polystyrenes, fluorinated aliphatic polymers, it being understood that said polymers must comprise proton-conducting groups, for example sulfonic acid, phosphonic acid or carboxylic acid groups.

In particular, the monomers may be:

ethylenic monomers bearing at least one sulfonic acid group, potentially in the form of a salt;

ethylenic monomers bearing at least one carboxylic acid group, potentially in the form of a salt; and ethylenic monomers bearing at least one phosphonic acid group, potentially in the form of a salt.

These monomers may be potentially fluorinated.

Even more particularly, these monomers may meet the following formula (II):

in which:

Z corresponds to a phenyl group; and

E corresponds to a proton-conducting group, potentially in the form of a salt, such as a sulfonic acid group, a phosphonic acid group or a carboxylic acid group.

A specific monomer meeting the definition given above is a styrene sulfonic acid monomer, for example in the form of a salt, such as a sodium salt (in which case, one could speak of sodium styrene sulfonate).

An example of this type of monomer is a monomer of following formula (III):

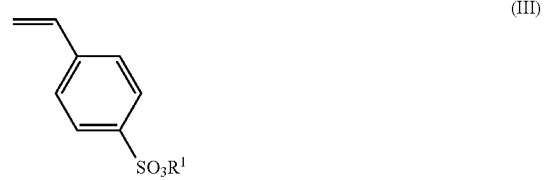

in which $R^1$ is a hydrogen atom or a cation (for example, a cation of alkaline metal).

As mentioned above, the polymerization step b) is governed by the mechanisms of ATRP polymerization, which operates on the principle of the reversible and rapid formation of species known as "dormant species" by creation of a covalent bond with the reactive radical species.

The reaction scheme for this type of polymerization may be illustrated by the following reaction scheme:

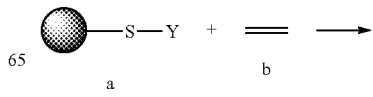

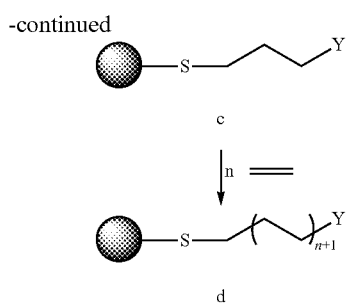

the group —S—Y schematically illustrating the radical of initiator compound bound to the surface of a particle (represented here by a full sphere), the compound=(indicated by b) illustrating a monomer.

As may be seen from this reaction scheme, the polymer chain grows by successive additions of monomers on free radicals, as in a conventional radical polymerization, the free radicals being created by departure of the Y group, which is then fixed after insertion of the monomer at the end of the polymer chain, which still constitutes a dormant species, which can continue to grow as long as monomers remain in the polymerization medium.

Apart from the presence of one or more monomers as defined above, the polymerization step b) takes place, conventionally, in the presence of a metal salt (for example, a metal halide, such as a copper halide, like copper chloride) and an organic ligand.

It is pointed out that organic ligand is taken to mean an organic compound comprising at least one free doublet capable of filling an electron vacancy of a metal element (to be specific, in our case, an electron vacancy on the metal element of the aforementioned salt) to form a metal complex.

As an example, a suitable organic ligand may be a compound belonging to the family of pyridine compounds, such as bipyridine.

The polymerization step b) may be carried out, moreover, in a water/organic solvent mixture (for example, an alcoholic solvent) under flow of an inert gas (such as a flow of argon) at a suitable temperature and for a suitable time to bring about polymerization.

After the polymerization step may follow one or more washing steps, in particular to eliminate the metal elements derived from the metal salt to carry out the polymerization (for example, by using a complexing solution, such as a solution of ethylenediaminetriacetate (EDTA)) and the monomers not having reacted.

The method of the invention may comprise, after the polymerization step, a step of hydrolysis intended to protonate the proton-conducting groups, when they are in the form of a salt (i.e., in other words, this step consists in replacing the cations of the salt by hydrogen atoms).

The average molar masses of the polymers obtained at the end of step b) may extend from 1000 to 1 000 000 g/mol, preferably 2000 to 200 000 g/mol.

A specific method according to the invention is a method, in which:
 the particles are platinum particles bound to a carbon material, of the carbon black type;
 the initiator compound is a compound of aforementioned formula (I);
 the monomer is a monomer of aforementioned formula (III).

The subject matter of the invention is also particles capable of being obtained by the method of the invention, namely particles comprising a material capable of catalyzing the reduction of oxygen or the oxidation of hydrogen, said particles being functionalized by polymers comprising at least one repeating unit having at least one proton-conducting group, said polymers being bound to said particles via a spacer group, which is a radical of a compound that is an initiator for ATRP polymerization bound in a covalent manner to said particles (the radical corresponding to the radical of initiator compound, after it has reacted, on the one hand, by means of one of its groups, with the particles to form a covalent bond and, on the other hand, by means of another of its groups with a monomer) whereby the polymers are bound in a covalent manner to the radical of initiator compound and said particles being, moreover, bound, for example, in a covalent manner, to a carbon material.

Such particles are particularly interesting, because they make it possible to transpose the phenomenology of the triple point to the molecular scale, the role of the catalyst being fulfilled by the material constituting the particle as such, the role of the proton conductor being fulfilled by the aforementioned polymers and the role of the electron conductor being fulfilled by the carbon material. The covalent bonds between the electron conductor and the catalyst on the one hand and between the proton-conducting material and the catalyst on the other hand assures, firstly, a better transfer of the charges (respectively, electrons and protons) and thus better performances and, secondly, perfect stability in fuel cell operating conditions, when said particles are used in fuel cells. These two results make it possible to reduce the catalyst load rate for increased performances.

As already mentioned for the method, the particles comprising a material capable of catalyzing the reduction of oxygen or the oxidation of hydrogen may be metal particles, namely particles comprising one or more metal elements (in which case, when there are several metal elements, one could speak of particles made of metal alloy(s).

Particularly suitable metal particles may be particles comprising a noble metal, such as platinum, ruthenium, palladium and mixtures thereof.

When the particles obtained according to the invention are intended to be used in PEMFC fuel cells, the metal particles are advantageously platinum particles.

The radicals of initiator compound may be radicals of an initiator compound as defined for the above method, in particular, a compound comprising a disulfide group —S—S— forming a bridge between two portions of said compound, at least one of said two portions comprising a phenyl group bearing an amide group —NH—CO—$R^1$, $R^1$ being a hydrocarbon group bearing at least one halogen atom (it is understood, in this case, the amide group is bound to a carbon atom of the phenyl group via the nitrogen atom of the group —NH—).

The polymers comprising at least one repeating unit bearing at least one proton-conducting group are similar to those already described for the above method and may be, in particular, polymers belonging to the family of polysulfones, polyetherketones, polyphenylenes, polystyrenes, fluorinated aliphatic polymers, it being understood that said polymers must comprise proton-conducting groups, for example sulfonic acid, phosphonic acid or carboxylic acid groups.

As for the carbon material, when it is present, it may be graphite, carbon black, carbon fibers, carbon tubes (such as carbon nanotubes), graphene and mixtures thereof.

As an example, when the particles are platinum particles, the initiator compound is a compound of formula (I), the monomer is a monomer of formula (III) and the carbon material is carbon black, the resulting particles are platinum particles, to which are bound, in a covalent manner, radicals of the initiator compound of following formula:

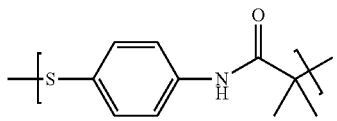

this radical being bound to the particles via the sulfur atom, the other end being bound to polymers comprising a sequence of repeating units derived from the polymerization of the monomer of formula (III). The average molar masses by weight of the polymers grafted onto the surface of the particles may extend from 1000 to 1 000 000 g/mol, ideally 2000 to 200 000 g/mol.

The ratio between the carbon material and platinum may be comprised between 80/20 and 20/80, ideally between 45/55 and 65/35.

The particles of the invention may enter into the constitution of electrodes for fuel cells, more particularly, for catalytic layers of PEMFC type fuel cells, as already mentioned above.

In fact, these particles are very stable up to 200° C. and have an electrochemical resistance up to 1 V vs RHE (RHE signifying reversible hydrogen electrode).

Thus, the invention also relates to a fuel cell device, for example of PEMFC type, comprising at least one electrode-membrane-electrode assembly, in which at least one of said electrodes is based on particles according to the invention.

The membrane for its part may be based on a proton-conducting polymeric material, the polymer(s) constituting said material being able to be of same nature as the polymer(s) grafted onto the surface of said particles.

Among the initiator compounds used within the scope of this invention, certain are novel, these initiator compounds being compounds comprising a disulfide group —S—S— forming a bridge between two portions of said compounds, at least one of these two portions comprising a phenyl group bearing an amide group —NH—CO—$R^1$, $R^1$ being a hydrocarbon group bearing at least one halogen atom (it is understood, in this case, that the amide group is bound to a carbon atom of the phenyl group via the nitrogen atom of the group —NH—).

The aforementioned two portions may be identical.

A particular compound meeting the definition given above may be a compound of formula (I) below:

(I)

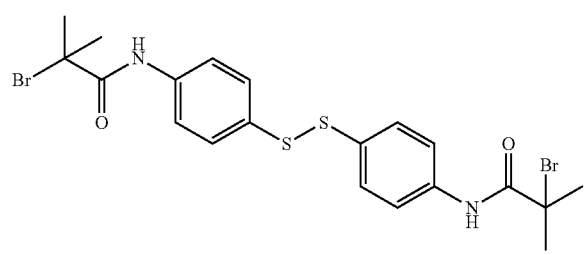

The invention will now be described, with respect to the following examples given by way of illustration and non-limiting.

DETAILED DESCRIPTION OF PARTICULAR EMBODIMENTS

Example 1

This example illustrates the preparation of the compound 2-bromo-N-{4-[4-(2-bromo-2-methylpropionylamino)-phenyldisulfanyl]-phenyl}-2-methylpropionamide of following formula (I):

(I)

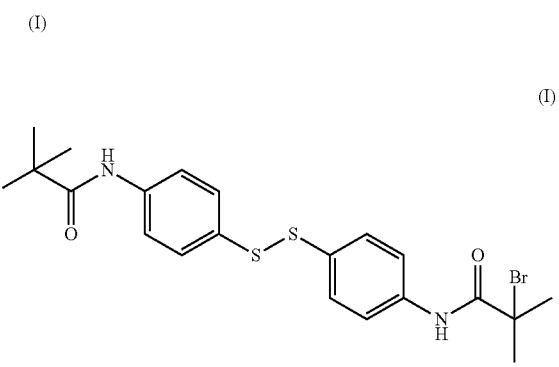

according to the following reaction scheme:

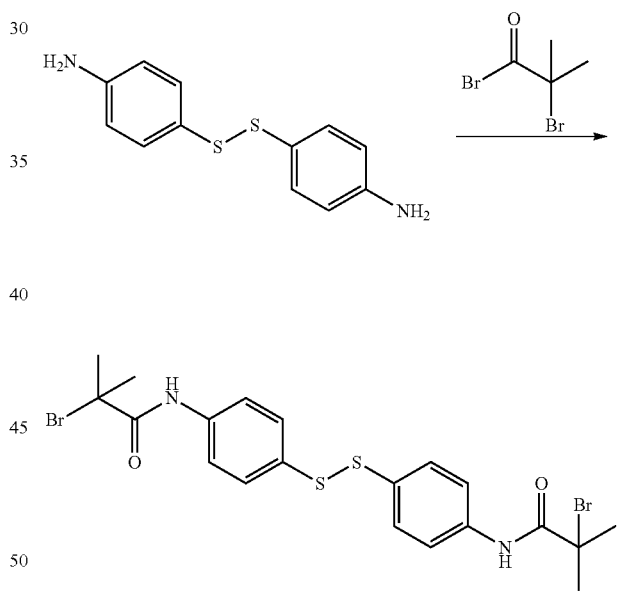

(I)

To do so, in a round bottomed flask equipped with a magnetic stirrer, 4-aminophenyl disulfide (248 mg; 1 mmol; 1 eq.) and bipyridine (343.6 mg; 2.2 mmol; 2.2 eq.) are dissolved in chloroform (10 mL). The reaction mixture is cooled by placing the round bottomed flask in a bath at 0° C. Bromoisobutyrate (272 μL; 2.2 eq.) is added drop by drop to the mixture thereby cooled. The resulting mixture is stirred for 10 hours, then the temperature is left to rise to room temperature. Water (10 mL) is poured into the round bottomed flask and the resulting mixture is then transferred into a separating funnel, so as to separate an aqueous phase and an organic phase.

The aqueous phase is washed with dichloromethane, whereby another organic phase is isolated.

The organic phases are combined then dried with magnesium sulfate (MgSO$_4$) then filtered. The resulting phase is then evaporated under vacuum in a rotating evaporator, so as to eliminate the organic solvents. The resulting product is purified on a chromatographic column on silica gel with, firstly, dichloromethane as eluent then, secondly, a dichloromethane/methanol mixture as eluent (90/10).

The resulting product (with a yield of 92%) corresponds to the expected product of formula (I) above according to 1H NMR spectroscopy, 13C NMR spectroscopy, IR spectroscopy analyses and elementary analysis, the results of which are given below.

$^1$H NMR (200.13 MHz, CDCl$_3$) δ: 8.47 (s, 1H, NH), 7.56-7.42 (m, 4H, H$_{arom}$), 2.04 (s, 6H, CH$_3$) ppm.

$^{13}$C NMR (200.13 MHz, CDCl$_3$) δ: 170.1 (C=O), 137.2 (NH—C$_{arom}$) 132.9 (S—C$_{arom}$), 130.1 (HN—C$_{arom}$—CH$_{arom}$—CH$_{arom}$—S), 120.6 (H2N—C$_{arom}$—CH$_{arom}$—CH$_{arom}$—S), 63.1 (Br—C—(CH$_3$)2, 32.6 (CH$_3$) ppm.

IR (cm$^{-1}$): 3300 (N—H), 1615 (C=O), 1086 (C—S), 570 (C—Br).

Elementary analysis (in %): (C20H22Br2N2O2S2), C, 42.5; H, 4.2; Br: 30; N, 4.3; O, 7.9; S, 11.1.

Example 2

This example illustrates the preparation of platinum particles bound to a carbon material, of carbon black type, (designated, in the formula below "Vulcan XC72"), represented by the formula below:

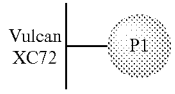

By a method involving a microemulsion known as "water-in-oil".

This preparation is conducted, in parallel, in two separate reactors. Into each reactor is poured heptane (18.71 g; 186.6 mmol) and Brij® 30 (5.30 g; 14.62 mmol). In parallel, a hexahydrated platinum salt H$_2$PtCl$_6$.6H$_2$O (275 mg; 0.212 mmol, 1 eq.) is dissolved in 2.5 mL of milliQ water. To each reactor is added 1 mL of the solution of metal salt then the whole is stirred so as to form a microemulsion. The resulting mixture is left to stand for a time extending from 15 to 20 minutes. Sodium borohydride (116 mg; 3.1 mmol; 15 eq.) is added by half to each reactor. The mixture turns from orange to intense black. After stirring, the remaining portion of sodium borohydride is added. The resulting mixture is stirred manually then left to stand for 30 minutes. The reduction reaction is considered as finished from the moment that there is no longer any release of gas. The contents of the two reactors are combined in a beaker, the latter being covered with aluminum foil then placed in an ultrasonic bath for 10 minutes. Vulcan®XC 72 carbon black (120 mg) is added to the beaker. The latter is placed back in an ultrasonic bath for 30 minutes. Once the beaker has been removed from the ultrasonic bath, acetone is added (1 volume of acetone for one volume of microemulsion). The mixture is left to stand for several minutes then is filtered on a membrane made of Durapore hydrophilic polyvinylidene fluoride (PVDF) (0.22 µm; GVWP 04700) under vacuum. The platinum particles supported on the carbon material (carbon black) are washed by filtration by cycles of 3*30 mL of acetone, 3*30 mL of an acetone/water (50/50) mixture, 3*30 mL of water firstly then, secondly, by series (at least three) of 2*30 mL of acetone, 1*30 mL of an acetone/water (50/50) mixture and 2*30 mL of water. The particles obtained are then placed overnight in an oven at a temperature of 75° C.

The yield is quantitative.

The particles obtained are analyzed by elementary analysis attesting to the presence of carbon (at a rate of 60%) and platinum (at a rate of 40%), which demonstrates that the platinum particles are supported on the carbon material.

Example 3

This example illustrates the preparation of platinum particles bound to a carbon material of carbon black type (designated, in the formula below, "Vulcan CX 72") by a method known as "instant method", said particles being able to be represented by the formula below:

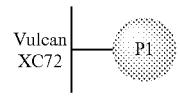

To do so, hexahydrated platinum salt H$_2$PtCl$_6$.6H$_2$O (259 mg; 0.50 mmol; 1 eq.) is dissolved in 10 mL of milliQ water, whereby a solution of metal salt is obtained. In parallel, in a 100 mL round bottomed flask equipped with a magnetic stirrer, lithium carbonate (111 mg; 1.5 mmol; 3 eq.) is dissolved in 30 mL of milliQ water. Vulcan®XC72 carbon material (146 mg) (corresponding to carbon black) is introduced into the round bottomed flask followed by the solution of metal salt. To obtain a final metal concentration of 10 mmol·L-1, 10 mL of water are added. The pH of the mixture is adjusted to a value of 9-10 by addition of lithium carbonate.

The reaction mixture is stirred at 500 rpm for 6 hours at 60° C. After 6 hours of reaction, the particles of platinum oxide obtained are reduced by addition of a 100 mmol·L-1 cold solution of sodium borohydride (NaBH4) (19 mg; 0.5 mmol; 1 eq.). The reduction step is carried out under a flow controlled by means of a pump, the output of which is set at 0.15 mL·min-1. Once returned to room temperature, the reaction mixture is filtered under vacuum then washed three times with milliQ water. The particles are recovered by filtration then are dried overnight in the oven at 75° C.

The yield is quantitative.

The particles obtained are analyzed by elementary analysis attesting to the presence of carbon (at a rate of 60%) and platinum (at a rate of 40%), which demonstrates that the platinum particles are supported on the carbon material.

Example 4

This example illustrates the preparation of platinum particles prepared according to the preceding examples grafted by the compound prepared in example 1, said grafted particles being able to be schematized by the formula below:

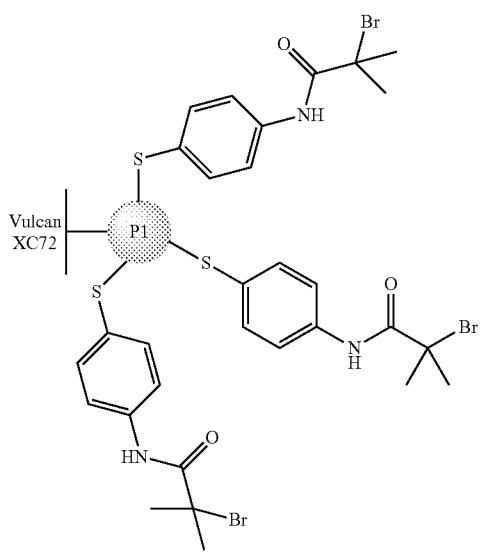

To do so, the platinum particles are suspended in 10 mL of hexylamine in a round bottomed flask equipped with a magnetic stirrer. The round bottomed flask is placed for 30 minutes in an ultrasonic bath, in order to obtain a dispersion of said particles. The compound of example 1 is dissolved in water then added to the round bottomed flask. The reaction mixture is stirred for 12 hours. The platinum particles are then washed and recovered by precipitation/centrifugation cycles, then dried overnight in an oven at 75° C.

Different tests have been conducted with different quantities of particles and the compound of example 1, these quantities being illustrated in table 1 below.

TABLE 1

| Particles (mg) | 98 | 96 | 94 | 92 | 90 | 88 | 86 | 84 | 82 | 80 |
|---|---|---|---|---|---|---|---|---|---|---|
| Compound example 1 (mg) | 4 | 8 | 12 | 16 | 20 | 24 | 28 | 32 | 36 | 40 |

Example 5

This example illustrates the preparation of platinum particles supported on a carbon material and grafted by a compound according to example 1, the grafting as such being carried out in the synthesis medium of the supported platinum particles (which enables this grafting to be qualified as in situ).

The particles thereby obtained may be schematized by the same formula as that represented in example 4.

To do so, this preparation is conducted, in parallel, in two separate reactors. Into each reactor is poured heptane (18.71 g; 186.6 mmol) and Brij® 30 (5.30 g; 14.62 mmol). In parallel, a hexahydrated platinum salt $H_2PtCl_6 \cdot 6H_2O$ (275 mg; 0.212 mmol, 1 eq.) is dissolved in 2.5 mL of milliQ water. To each reactor is added 1 mL of the solution of metal salt then the whole is stirred so as to form a microemulsion. The resulting mixture is left to stand for a time extending from 15 to 20 minutes. Sodium borohydride (116 mg; 3.1 mmol; 15 eq.) is added by half to each reactor. The mixture turns from orange to intense black. After stirring, the remaining portion of sodium borohydride is added. The resulting mixture is stirred manually then left to stand for 30 minutes. The reduction reaction is considered as finished from the moment that there is no longer any release of gas. The compound prepared in example 1 dissolved beforehand is added to each reactor. The reactors are placed under stirring for 1 hour. The contents of the two reactors are combined in a beaker, the latter being covered with aluminum foil then placed in an ultrasonic bath for 10 minutes. Vulcan®XC 72 carbon black (120 mg) is added to the beaker. The latter is placed back in an ultrasonic bath for 30 minutes. Once the beaker has been removed from the ultrasonic bath, acetone is added (1 volume of acetone for one volume of microemulsion). The mixture is left to stand for several minutes then is filtered on a membrane made of Durapore hydrophilic polyvinylidene fluoride (PVDF) (0.22 µm; GVWP 04700) under vacuum. The platinum particles bound to the carbon material (carbon black) are washed by filtration by cycles of 3*30 mL of acetone, 3*30 mL of an acetone/water (50/50) mixture, 3*30 mL of water firstly then, secondly, by series (at least three) of 2*30 mL of acetone, 1*30 mL of an acetone/water (50/50) mixture and 2*30 mL of water. The particles obtained are then placed overnight in an oven at a temperature of 75° C.

Different tests have been conducted with different quantities of Vulcan XC®72 and the compound of example 1, these quantities being explained in table 2 below.

TABLE 2

| Vulcan ® XC72 (mg) | 58 | 56 | 54 | 52 | 50 | 48 | 46 | 44 | 42 | 40 |
|---|---|---|---|---|---|---|---|---|---|---|
| Compound example 1 (mg) | 4 | 8 | 12 | 16 | 20 | 24 | 28 | 32 | 36 | 40 |

Example 6

This example illustrates the polymerization of sodium styrene sulfonate from platinum particles prepared according to the preceding examples, the particles thereby obtained being able to be represented by the formula below:

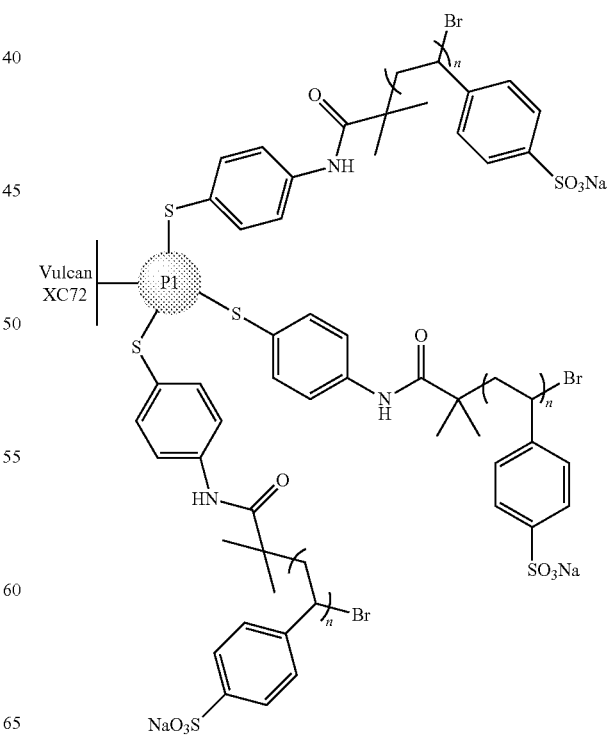

n corresponding to the number of repetitions of the unit taken between brackets.

To do so, in a two-necked flask equipped with a magnetic stirrer, the grafted platinum particles prepared beforehand (1 eq.) are dispersed in a water/methanol (3/1) mixture by means of an ultrasonic bath (for 1 hour). The reaction mixture is degassed through the application of vacuum/argon cycles. Copper chloride (4 eq.) and 2,2'-bipyridine (8 eq.) are added to the mixture under argon flow. Sodium styrene sulfonate is added to the dispersion under stirring and under argon flow. After 20 hours of polymerization, the reaction is stopped by exposing the reaction medium to air. The platinum particles thereby functionalized are recovered and washed by several centrifugation cycles using a solution of EDTA (2*10 g·L-1) and milliQ water (2 times), in order to eliminate Cu2+ ions and the remaining monomers. The product obtained is dried in an oven overnight at 75° C.

Different tests have been implemented so as to obtain a targeted molar mass, the quantities of monomers required to obtain the targeted molar mass being indicated in table 3 below.

TABLE 3

| Targeted molar mass (g · mol − 1) | Number of equivalents of monomer |
|---|---|
| 10 000 | 48 |
| 50 000 | 240 |
| 100 000 | 480 |

The particles obtained have been tested by thermogravimetric analysis, so as to estimate the thermal resistance thereof, this analysis having been carried out under air with a variation of temperatures ranging from 25° C. to 800° C.

The analysis highlights that, up to 200° C., no degradation is visible, which makes it possible to envisage the use of these particles as entering into the constitution of catalytic layers of electrodes for fuel cells.

The electrochemical characteristics of the particles obtained above were also determined.

In particular, the characterization was carried out of the resistance of the organic crown in support medium (the organic crown corresponding to the polymers grafted to the particles via the radicals of initiator compound) with a cell with three electrodes. In this cell, the reference electrode is a reversible hydrogen electrode (RHE) in which the electrochemical potential is fixed and known. The second electrode is an auxiliary electrode known as counter electrode (CE) constituted of an inert material, a wafer of vitreous carbon in our case, and which serves for current collection. The third electrode is a working electrode (WE) on which is situated the studied catalyst. A gas input and output system (AG/SG) is added in order to work in controlled atmosphere. The characterization of this resistance was carried out by cycling of the electrode potential between 0.05 V vs RHE (RHE signifying reference hydrogen electrode) and an upper potential limit successively equal to 0.55 V vs RHE (only faradic phenomena of adsorption/desorption of hydrogen occurring over this potential range, the currents recorded between 0.4 V and 0.55 V vs RHE being due to the phenomenon of double layer capacitance), 0.8 V vs RHE (potential situated just before the start of the reaction of oxidation of the platinum), 1.0 V vs RHE (potential situated after the start of the reaction of oxidation of the platinum, and corresponding to the potential of a cathode of a PEMFC type fuel cell in open circuit) and 1.2 V vs RHE (highly oxidizing potential).

It turns out that, for electrode potentials above 1.0 V vs RHE, the currents observed in the adsorption/desorption zone increase until current values recorded on an electrode based on platinum particles uniquely bound to a carbon material (Vulcan XC72) are obtained. This observation shows that the organic crown, bound to the platinum, is stable up to applied potentials of 1.0 V vs RHE.

The characterization was also carried out of the particles of the invention in oxygen-saturated acid medium, so as to study their catalytic behavior vis-à-vis the oxygen reduction reaction. The appearance of the voltammograms obtained is equivalent to that obtained for catalysts constituted of platinum particles uniquely bound to a carbon material (Vulcan XC72/Pt). The total number of exchanged electrons is equal to 4 between 0.7 and 0.4 V vs RHE. The reduction of oxygen is thus complete to form water.

Finally, the selectivity of the particles of the invention has been determined, this selectivity being able to be defined as the capacity of a catalyst to transform precise reagents into one or more given products, which are, in this case, for the reduction of oxygen: water and hydrogen peroxide. It has been determined that hydrogen peroxide is only produced from 0.8 V vs RHE.

This implies a direct reduction of oxygen into water in the range of potentials extending from 1.1 to 0.8 V vs RHE. For lower potentials, the proportion of peroxide rises to 5%, which is entirely compatible with a fuel cell use.

What is claimed is:

1. Method for preparing platinum particles being functionalized by polymers comprising at least one repeating unit bearing at least one proton-conducting group and being covalently bonded to a carbon material, said method comprising the following consecutive steps:
    a) a step of contacting platinum particles with a compound that is an initiator for ATRP polymerization, which compound comprising a disulfide group —S—S— forming a bridge between two portions of said compound, said two portions being identical and comprising a phenyl group bearing an amide group —NH—CO—R$^1$, R$^1$ being a hydrocarbon group having at least one halogen atom, whereby particles, onto which a radical of said initiator compound is grafted, are obtained;
    b) a step of contacting said particles obtained in a) with at least one monomer meeting the following formula (II):

(II)

in which:
—Z corresponds to a phenyl group; and
—E corresponds to a proton-conducting group,
whereby there is polymerization of said monomer from the above-mentioned radicals.

2. Method according to claim 1, in which the initiator compound is a compound of following formula (I):

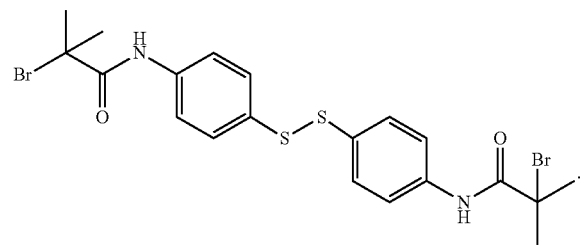
(I)

3. Method according to claim 1, comprising, before step a), a step of preparing particles comprising a material capable of catalyzing the reduction of oxygen or the oxidation of hydrogen.

4. Method according to claim 1, in which the carbon material is selected from graphite, carbon black, carbon fibers, carbon tubes, graphene and mixtures thereof.

5. Method according to claim 1, further comprising, before step a), a step of preparing particles comprising a material capable of catalyzing the reduction of oxygen or the oxidation of hydrogen bound to a carbon material.

6. Method according to claim 1, comprising, after step a) and before step b), a step of contacting the particles obtained at the end of step a) with the carbon material, whereby said particles are bound, at the end of said contacting step, to the carbon material.

7. Method according to claim 1, wherein the proton-conducting group is in the form of a salt selected from the group consisting of: a sulfonic acid group, a phosphonic acid group and a carboxylic acid group.

8. Method according to claim 7, in which the monomer is a monomer of following formula (III):

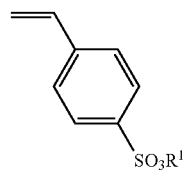
(III)

in which $R^1$ is a hydrogen atom or a cation.

9. Method according to claim 1, in which:
the particles are platinum particles bound to a carbon material, of carbon black type;
the initiator compound is a compound of the following formula (I):

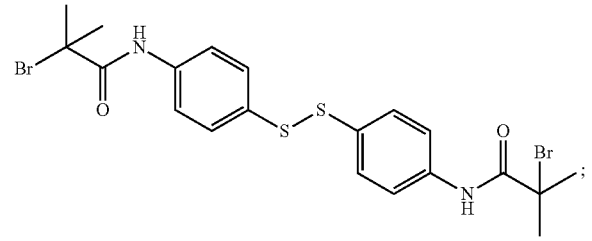
(I)

and
the monomer is a monomer of the following formula (III):

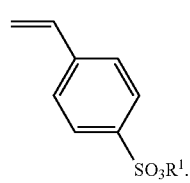
(III)

* * * * *